United States Patent [19]

Kamber et al.

[11] 4,271,068

[45] Jun. 2, 1981

[54] PROCESS FOR THE MANUFACTURE OF CYSTINE-CONTAINING PEPTIDES

[75] Inventors: Bruno Kamber; Werner Rittel, both of Basel, Switzerland

[73] Assignee: Ciba-Geigy Corporation, Ardsley, N.Y.

[21] Appl. No.: 685,857

[22] Filed: May 13, 1976

Related U.S. Application Data

[63] Continuation of Ser. No. 296,406, Oct. 10, 1972, which is a continuation-in-part of Ser. No. 818,109, Apr. 21, 1969, abandoned.

[51] Int. Cl.$^2$ ............................................ C07C 103/52
[52] U.S. Cl. ............................................ 260/112.5 R
[58] Field of Search ................................ 260/112.5 R

[56] References Cited

FOREIGN PATENT DOCUMENTS 2060969 12/1969 Fed. Rep. of Germany .... 260/112.5 R

OTHER PUBLICATIONS

J. Am. Chem. Soc. 87, 4922–4933, (1965).
J. Am. Chem. Soc. 74, 1862–1863, (1952).
J. Am. Chem. Soc. 90, 2677–2681 (1968).
Chem. Ber. 101, 681–693, (1968).
Bull. Chem. Soc. Jap. 37, 433–434, (1964).
J. Org. Chem. 31, 1192–1195, 1966).
J. Am. Chem. Soc. 84, 4789–4794, (1962).

*Primary Examiner*—Delbert R. Phillips
*Attorney, Agent, or Firm*—Prabodh I. Almaula

[57] ABSTRACT

The invention concerns an improved process for the manufacture of cystine-containing peptides from cysteine-containing aminoacid sequences whose mercapto groups are protected by trityl groups, wherein the S-trityl cysteine-containing sequences are directly oxidized with iodine to yield the cystine disulfide bond.

9 Claims, No Drawings

PROCESS FOR THE MANUFACTURE OF CYSTINE-CONTAINING PEPTIDES

CROSS-REFERENCE TO RELATED APPLICATIONS

The present application is a continuation of application Ser. No. 296,406, filed Oct. 10, 1972, which, in turn, is a continuation-in-part of our application Ser. No. 818,109, filed Apr. 21, 1969 (now abandoned).

The present invention provides a new process for the manufacture of cystine-containing peptides.

Various cystine-containing peptides occur in nature in which the disulphide bridge of cystine is located in a ring, for example oxytocin, vasopressins, vasotocin, isotocin, mesotocin, growth hormone, thyrocalcitonin and insulin. However, the disulphide bridge of cystine may also connect linear aminoacid chains as is the case, for example, with the two disulphide bridges between the chains A and B of insulin or with glutathione. At this stage various methods are known for the synthesis of peptides containing such disulphide bridges. Apart from natural peptides with disulphide bridges a considerable number of active analogues have already been synthesized, for example desamino-oxytocin, $Ser^4$-oxytocin, $Asn^4$-oxytocin, $Val^8$-oxytocin, $Tyr^2$(O-methyl)-oxytocin, $Phe^2$-$Arg^8$-vasopressin, $Phe^2$-$Lys^8$-vasopressin, $Phe^2$-$Orn^8$-vasopressin, $Ile^3$-$Arg^8$-vasopressin and $Asn^4$-$Lys^8$-vasopressin.

According to the known process for the manufacture of the disulphide bridge the mercapto protective groups are eliminated from an aminoacid sequence containing the two cysteine residues to be connected, in which the mercapto groups are protected, for instance by carbobenzoxy or benzyl groups or by the trityl group (the benzyl groups, for example, with sodium in liquid ammonia, the trityl group, for example, by means of mercuric acetate and hydrogen sulphide or with 10 N-hydrochloric acid) and the peptide containing the free mercapto groups is then oxidized to the disulphide, for example with 1,2-diiodoethane or with oxygen. This process has the disadvantage that the said eliminating methods give rise to side-reactions, more especially in the case of sensitive peptide which reduce the yield correspondingly. The present invention is based on the observation that cystine-containing peptides and their derivatives are obtained in a simpler and more careful manner and in better yield when the aminoacid sequence(s) containing the cysteine residues to be connected, in which the mercapto groups are protected by trityl groups, is/are treated with iodine. The reaction is performed at room temperature but, depending on the type of peptide concerned, it may also be carried out at a lower or higher temperature, for example at a temperature ranging from $-50$ to $+150°$ C., preferably from $0°$ to $60°$ C. It is advantageous to perform the reaction in a solvent or mixture of solvents in which both iodine and the peptide are at least partially soluble. As such solvents there are to be mentioned in the first line water, glacial acetic acid or alkohols such as lower alkanols, for example ethanol or especially methanol, or mixtures of these solvents, or mixtures with other organic solvents for iodine and the peptide, for instance esters such as esters of lower alkanoic acids with lower alkanols, e.g. ethyl acetate, or amides, such as unsubstituted or N-substituted, especially N-lower alkyl- or N,N-dilower alkyl-substituted amides of lower alkanoic acids, for example formamide or dimethylformamide, or amides of phosphoric acid, for example hexamethylphosphoric acid amide, or halogenated, especially chlorinated hydrocarbons having at most 6 carbon atoms, for instance methylene chloride, chloroform, carbon tetrachloride, ethylene dichloride, ethylene tetrachloride.

The solution may have a pH value of about 0 to 9, preferably 2 to 7. There are used at least one, usually about one to three mols of iodine pro mol of cystine peptide. If open-chain cystine peptides are to be prepared, the reaction is preferably performed by mixing, in any desired manner, a solution of the cysteine peptide with a solution of iodine containing for instance 1.2 to 3.5 mols of iodine pro mol of cystine peptide. In the case of cyclic cystine peptides, it is appropriate to work in such a way that an excess of iodine (3 to 20 mols) is present during the whole reaction time, for example by working in a dilute peptide solution (e.g. 0.2 to 10 mmols of peptide pro liter) and adding the peptide solution to the iodine solution. The excess iodine can be removed from the resulting solution, for example, with thiosulphate.

The reaction takes place within about 1 to 180 minutes, usually within 10 to 60 minutes.

If the process is to be used for the manufacture of cystine-peptides which, to permit further condensation at the amino group, carry protective groups that are easily split off by acids such, for example, as trityl or 2-(p-biphenylyl)-2-propyloxycarbonyl (compare French Patent No. 1 554 051), or equivalent groups, the process is advantageously carried out in the presence of acid acceptors or buffers. Acid acceptors that may be used are, for example (especially if the reaction is carried out in aqueous solution) weak alkalies, for example, sodium carbonate or sodium bicarbonate or, chiefly in organic solution, organic nitrogen bases such as primary, secondary or tertiary amines, for example appropriate lower alkyl- or cycloalkylamines, aromatic, araliphatic or heterocyclic amines, for example sec. butylamine, morpholine, thiomorpholine, pyrrolidine, piperidine, aniline, toluidine, benzylamine, triethylamine, Hunig base, quinoline, preferably pyridine. As buffers may be mentioned those with a pH range of 4.5 to 9, preferably 5–8, for example, alkali metal salts of weak acids, such as acetate buffer, citrate buffer, phosphate buffer. In the synthesis of peptides containing cystine with the use of protective groups that can be split off by acids, the $\alpha$-amino group, for example, can be protected by the trityl or 2-(p-biphenylyl)-2-propyloxycarbonyl group and the side chain amino groups can be protected by the tert.butoxycarbonyl group, and, further, hydroxyl groups can for example be protected by the tert.butyl ether group and carboxyl groups by the tert.butyl ester group. On oxidation to give the cystine, the $N^\alpha$-trityl or 2-(p-biphenylyl)-2-propoxycarbonyl group is then not attacked. These $N^\alpha$-groups can subsequently to the oxidation be split off selectively relative to the remaining protective groups by means of an acid, for example with 80% strength acetic acid, and the resulting protected peptide with a free $\alpha$-amino group can be used for the further condensation.

In the process according to the invention, cysteine peptides in which the amino groups are free or protected are used as starting substances. Free hydroxyl, carboxyl and guanidino groups can also, if desired, be present in a protected form. As amino protective groups there should be mentioned, for example, trifluoracetyl, phthaloyl, p-toluenesulphonyl, or above all groups derived from carbonic avid such as aromatic, araliphatic or aliphatic oxycarbonyl groups. In the aromatic and araliphatic groups the aromatic residue is preferably phenyl which is unsubstituted or substituted by halogen such as chlorine or bromine, by lower alkyl or lower alkoxy or nitro or by optionally substituted phenylazo groups. The aliphatic residue in araliphatic oxycarbonyl groups is preferably lower alkyl. Examples are tolyloxycarbonyl, benzyloxycarbonyl, p-methoxy-benzyloxycarbonyl, p-nitro-benzyloxycarbonyl, p-methoxyphenylazo-benzyloxycarbonyl, p-phenylazo-benzyloxycarbonyl, p-chlorobenzyloxycarbonyl, 2-phenylisopropyloxycarbonyl, 2-p-tolyl-isopropyloxycarbonyl, 1,1-diphenylethyloxycarbonyl and above all 2-(p-biphenylyl)-2-propyloxycarbonyl. Aliphatic oxycarbonyl groups are especially lower alkyl or halogeno-lower alkyl or saturated cyclic groups having at most 10 carbon atoms, for example, cyclopentyloxycarbonyl, cyclohexyloxycarbonyl, adamantyloxycarbonyl, 2,2,2-trichlorethoxycarbonyl, 2-chlorethoxycarbonyl, tert.amyloxycarbonyl and primarily tert.butyloxycarbonyl.

The reaction can also be carried out if the amino groups are present in the form of salts, for instance hydrochlorides.

If desired, the carboxyl groups may be protected or functionally converted, especially by amidation or esterification. The amides may be N-unsubstituted or N-mono- or disubstituted. Substituents are for instance alkyl groups having 1-18, especially 1-5 carbon atoms. Suitable esters are, for example, those of lower alkanols or halogenated, especially chlorinated lower alkanols or monocyclic aryl lower alkanols such as phenyl lower alkanols which are unsubstituted or substituted by halogen, lower alkyl, lower alkoxy, trifluoromethyl or nitro in the phenyl ring, or of phenols which may be substituted in the same way as the phenyl lower alkanols. Examples for such esterifying hydroxy compounds are methanol, ethanol, propanol, tertiary butanol, tertiary amylalcohol, 2-chlorethanol, 2,2,2-trichlorethanol, benzyl alcohol, p-nitro- benzylalcohol, p-methoxybenzyl alcohol, p-nitrophenol, 2,4-dinitrophenol, 2,4,6-trinitrophenol, 2,4,5-trichlorphenol, 2,3,4,5,6-pentachlorphenol. Other functionally converted carboxyl groups are for instance esters obtained with N-hydroxy-succinimide or N-hydroxyphthalimide and other activated esters as mentioned for instance in U.S. Pat. No. 3,035,041.

Hydroxyl groups, for example of serine or tyrosine, may be protected, for example, by etherification, for instance with benzyl alcohol or preferably with tertiary butanol. If cystine-peptides containing tyrosine are prepared according to the new process in an aqueous solvent the hydroxyl group of tyrosine has to be protected to avoid iodation.

The guanidino group in arginine residues may be protected, if desired, for example by the tosyl group. Further protective groups for amino, carboxyl, hydroxy and guanidino groups are described, for instance, in the text book "The Peptides" of Schroder and Lubke, Academic Press, New York and London, Vol. I and II, 1965-66.

The disulphide-peptides containing protective groups obtained by the present process may be used as they are for the synthesis of peptides having a longer aminoacid chain or, if desired, the protective groups may be eliminated in known manner, for example with acids such as mineral acids, e.g. hydrochloric or hydrofluoric acid, or organic acids, for instance trifluoracetic acid.

The reaction can also be carried out if the carboxyl groups are present as salts, for example as salts with alkali metals, ammonia or organic nitrogen bases, for example ethanolamine, diethylamine, triethylamine, tributylamine, pyridine or pyrrolidine. The cysteine-peptides and their derivatives used as starting materials are known or can be prepared by known methods. The term cysteine-peptides means peptides which contain at least one cysteine residue. Peptides are above all naturally occurring peptides and synthetic analogues thereof, as well as part-sequences of such peptides. These peptides are built up of naturally occurring aminoacids, above all of the 20 code-aminoacids, and also of their homologues, structural isomers and optical isomers; the peptides can contain amino-lower alkanoic acids with 3-7 carbon atoms, such as $\beta$-alanine, $\alpha$-aminobutyric acid, $\gamma$-aminobutyric, $\alpha,\beta$-diaminopropionic acid, norvaline, norleucine and also, for example, hydroxyproline, normethionine, phenylglycine, ornithine, citrulline O-methyl-tyrosine or N-alkyl-aminoacids such as N-methyltyrosine, or corresponding D-compounds. By derivatives there are especially to be understood peptides in which functional groups, such as amino, carboxyl, hydroxyl and/or guanidino groups are protected or functionally converted as mentioned above. Furthermore, by derivatives are embraced compounds which instead of one or both of the cysteine residues to be bonded contain desamino-cysteine residues.

The following Examples illustrate the invention. In thin-layer chromatography the following systems are used:

System 43A = tertiary amyl alcohol + isopropanol + water (51:21:28)
   43C = tertiary amyl alcohol + isopropanol + water (51:21:28)
   45 = secondary butanol + 3% aqueous ammonia (70:30)
   52 = n-butanol + glacial acetic acid + water (75:7.5:21)
   53 = n-butanol + formic acid + water (60:0.75:39)
   70 = ethyl acetate + pyridine + water (40:20:40)
   101 = n-butanol + pyridine + glacial acetic acid + water (38:24:8:30)
   102E = ethyl acetate + methylethylketone + glacial acetic acid + water (50:30:10:10)
   121A = isopropanol + 26% ammonia + water (85:5:10)

The following abbreviations are used:
BOC = tertiary butoxycarbonyl,
TRI = trityl.

Example 1 illustrates the manufacture of the protected N-terminal sequence 1-9 of thyrocalcitonin with disulphide ring. Examples 2 and 8 illustrate the disulphide linking of the protected fragment 20-21 of the A-chain with the protected fragment 18-21 or 19-21 of the B-chain of insulin. Examples 3, 7 and 9 illustrate the manufacture of protected peptide dimers with a disulphide bridge. Examples 4-6 illustrate the manufacture of oxytocin, Lys$^8$-vasopressin and Phe$^2$, Lys$^8$-vasopressin by the new process.

The peptides obtainable by the process of the invention have a known utility or are intermediates for the manufacture of peptides with known utility. Thus, for instance, the protected N-terminal sequence 1-9 of $\alpha$-thyrocalcitonin can be condensed with the sequence 10-32 of that peptide to form the protected α-thyrocalcitonin from which the protective groups are split off to yield free α-thyrocalcitonin, as described, for example, appln. Ser. No. 034,471 by Max Brugger et al. filed Nov. 6, 1968. The protected fragment of aminoacids 20-21 of the A-chain of insulin linked by the disulfide bridge to the protected fragment 18-21 or 19-21 of the B-chain of insulin can be converted by splitting of the protective groups to the corresponding free peptides which boost the action of insulin as has been found from in vitro tests on isolated embryonic chicken extremity cartilages. The mentioned protected linked fragments of the A- and B-chain of insulin are new and form also a subject of the present application.

EXAMPLE 1

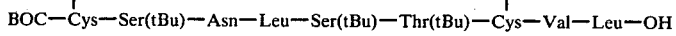

BOC—Cys—Ser(tBu)—Asn—Leu—Ser(tBu)—Thr(tBu)—Cys—Val—Leu—OH 2.50 Grams (1.478 mmols) of BOC-Cys(TRI)-Ser(tBu)Asn-Leu-Ser(tBu)-Thr(tBu)-Cys(TRI)-Val-Leu-OH in 500 ml of methanol are dropped within 45 minutes into a stirred solution of 3.73 g (14.78 mmols) of iodine in 500 ml of methanol at room temperature. On completion of the addition the batch is stirred on for 1 hour and the solution is then decolorized at 0° C. with N-aqueous thiosulphate solution (26.05 ml of N-thiosulphate). The clear solution is concentrated to about 100 ml under a water-jet vacuum at 30° C., then 1.5 liters of water are added, and the precipitated product is filtered off and washed with water. After drying over potassium hydroxide the crude product weighs 2.32 g; it is twice triturated with petroleum ether and purified by counter-current distribution in the system methanol+-buffer+chloroform+carbon tetrachloride (10:3:5:4). [Buffer: 28.6 ml of glacial acetic acid; 19.25 g of ammonium acetate, made up to 1 liter with water.] After 135 steps the main product is found in elements 39-68 ($r_{max}$=53; K=0.65). The contents of these elements are combined and evaporated to dryness under a high vacuum at 40° C., and the ammonium acetate is sublimed. The resulting

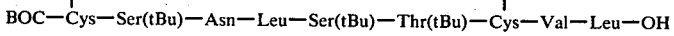

BOC—Cys—Ser(tBu)—Asn—Leu—Ser(tBu)—Thr(tBu)—Cys—Val—Leu—OH (1.49 g=83% of theory) proves to be unitary in thin-layer chromatography on silicagel. $Rf_{45}$=0.42; $Rf_{121A}$=0.70; $Rf_{70}$=0.75; $Rf_{53}$=0.43; $Rf_{43A}$=0.22. Optical rotation $[\alpha]_D^{23}$=−16° (c=2 in chloroform). The protected nonapeptide used as starting material can be prepared by the process described in appln. Ser. No. 034,471 by Max Brugger et al. filed Nov. 6, 1968, as follows:

(1) H-Thr(tBu)-OMe 12.92 Grams (40 mmols) of Z-Thr-(tBu)-OMe in 200 ml of glacial acetic acid and 3 g of palladium carbon (10% Pd) are hydrogenated at room temperature. The absorption of hydrogen ceases after one hour. The catalyst is filtered off and the filtrate evaporated at 35° C. in a water-jet vacuum. The residue is dried in a high vacuum at 35° C. and yields 7.3 g of an oil which is unitary according to its thin-layer chromatogram and can be further used as it is.

(2) DPC-Ser(tBu)-Thr(tBu)-OMe 19.3 Grams (38.6 mmols) of DPC-Ser(tBu)-OH (cyclohexylamine salt) are taken up in 500 ml of chloroform and agitated at 0° C. three times with 25 ml of N-citric acid and 5 times with 40 ml of semisaturated sodium chloride solution. The solution is dried over sodium sulphate and evaporated and the resulting foam is taken up in 250 ml of ethyl acetate. Then 5.36 ml (38.6 mmols) of triethylamine are added, the solution is cooled to −10° C. and 5.13 ml (38.6 mmols) of isobutylchlorocarbonate are stirred in. The solution is stirred for 10 minutes at −10° C. and a solution, cooled to −12° C., of 7.3 g (38.6 mmols) of H-Thr(tBu)-OMe in 100 ml of ethyl acetate is dropped in so that the reaction temperature never rises above −10° C. On completion of the dropwise addition the batch is stirred on for 1 hour at −10° C. and then left to itself overnight at room temperature. The precipitated triethylamine hydrochloride is filtered off and the solution washed at 0° C. with 3×20 ml of N-citric acid and 5 times with saturated sodium chloride solution, dried and evaporated. Yield of crude product (oil): 22.07 g. For purification 1 g is chromatographed on a silica gel column (2.5 cm, 30 cm). Elution with petroleum ether+ethyl acetate (1:1) furnishes after a fore-running of 110 ml 787 mg of pure product. It reveals an Rf value of 0.51 in the thin-layer chromatogram on silica gel in toluenme+acetone (7:3).

(3) Z-Val-Leu-OMe

A solution of 19.9 g (110 mmols) of H-Leu-OMe.HCl in 120 ml of dimethylformamide is mixed at 0° C. with 14.6 ml (105 mmols) of triethylamine. The precipitated triethylamine hydrochloride is filtered off, the filtrate added to a solution of 25.1 g (100 mmols) of Z-Val-OH in 200 ml of dimethylformamide at 0° C. and then 22.6 g (110 mmols) of dry dicyclohexylcarbodiimide are added. The batch is stirred for 1 hour at 0° C., then kept overnight in a refrigerator, filtered, and the filtrate is evaporated under a high vacuum at 40° C. The oily residue is taken up in 30 ml of ethyl acetate, the solution cooled to 0° C. and the precipitated dicyclohexylurea is filtered off. On addition of n-hexane the product crystallizes overnight out of the filtrate; it melts at 102°-105° C. Optical rotation $[\alpha]_D^{20}$=−41° (c=2.88 in methanol).

In the thin-layer chromatogram on silica gel in chloroform+methanol (98:2) the Rf value is 0.55 and in toluene+acetone (7:3) it is 0.60.

(4) DPC-Ser(tBu)-Thr(tBu)—NH—NH₂

A mixture of 4.253 g (7.4 mmols) of DPC-Ser(tBu)-Thr(tBu)-OMe in 18 ml of methanol is mixed with 5.55 ml (about 110 mmols) of hydrazine hydrate, and then kept for 10 hours at room temperature and 2 hours at 40° C. The reaction solution is taken up in 450 ml of ethyl acetate and four times washed with semisaturated sodium chloride solution, dried over sodiumsulphate, concentrated to about 15 ml and about 5 ml of petroleum ether are added. Overnight 3.17 g of the hydrazide, melting at 132°–134° C., crystallize out.

In the thin-layer chromatogram on silica gel in toluene+acetone (7:3) Rf=0.40.

(5) H-Val-Leu-OMe,HCl 5.66 Grams (15 mmols) of Z-Val-Leu-OMe in 75 methanol are hydrogenated in the presence of 15 mmols of hydrochloric acid and 850 mg of palladium carbon (10%Pd) at room temperature. The adsorption of hydrogen ceases after 3 hours. The catalyst is filtered off and the filtrate concentrated to about 15 ml. On addition of ether the product, melting at 136°–139° C., crystallizes out. In the thin-layer chromatogram on silica gel in chloroform+methanol (9:1) Rf=0.45 and in toluene+acetone (1:1) Rf=0.43.

(6) TRI-Cys(TRI)-Val-Leu-OMe 7.13 Grams (10 mmols) of TRI-Cys(TRI)-OH (diethylamine salt are washed in chlororm at 0° with N-citric acid and semisaturated sodium chloride solution; the solution is dried, evaporated and the resulting foam is taken up in 50 ml of ethyl acetate, then a solution of 3.22 g (10 mmols) of H-Val-Leu-OMe hydrochloride in 40 ml of ethyl acetate of 0° C., mixed with 1.4 ml (10 mmols) of triethylamine from which the precipitated triethylamine hydrochloride has been filtered off, is added. Then 2.26 g (11 mmols) of dry dicyclohexylcarbodiimide are added at 0° C., the whole is stirred for 2½ hours at 0° C. and kept overnight in a refrigerator. The precipitated dicyclohexylurea is filtered off and the solution washed at 0° C. with N-citric acid, N-sodium bicarbonate and semisaturated sodium chloride solution and dried over sodium sulphate. The solution is concentrated to about 20 ml, cooled to 0° C., and further dicyclohexylurea is filtered off. Evaporation to dryness furnishes 8.53 g of ester. For purification the crude product is chromatographed on a silica gel column (5 cm; 55 cm). After a fore-running of 400 ml the main product is eluted in pure form with 300 ml of petroleum ether+ ethyl acetate (1:1). In the thin-layer chromatogram on silica gel in chloroform+methanol (99:1) Rf=0.43.

(7) H-Cys(TRI)-Val-Leu-OMe 12.3 ml of water are dropped into a solution of 11.08 g (13.3 mols) of TRI-Cys(TRI)-Val-Leu-OMe in 75 ml of ethyl acetate so that at all times the solution remains clear. After 1 hours' stirring at room temperature the clear solution is mixed with 64 ml of water, filtered to remove the precipitate and washed with cold 50% acetic acid. The filtrate is evaporated under a high vacuum at 40° C. to leave an oil which is taken up in 250 ml of ethyl acetate, washed at 0° C. with N-sodium bicarbonate and saturated sodium chloride solution, dried over sodium sulphate and evaporated to yield 7.07 g of a white product. When the thin-layer chromatogram on silica gel in chloroform+methanol (98:2) is sprayed with Reindel-Hoppe reagent, there appears a stain of Rf=0.30.

(8) DPC-Ser(tBu)-Thr(tBu)-Cys(TRI)-Val-Leu-OMe 13.6 Grams (23.8 mmols) of DPC-Ser(tBu)-Thr(tBu)-NH—NH$_2$ in 220 ml of dimethylformamide are mixed at −12° C. with 32.26 ml of hydrochloric acid in ethyl acetate (1.84 N; 59.25 mmols) and 3.26 ml (28.55 mmols) of tertiary butylnitrite. After 15 minutes at −10° C. a solution, cooled at −10° C., of 14.03 g (23.8 mmols) of H-Cys(TRI)-Val-Leu-OMe and 8.315 ml (59.25 mmols) of triethylamine in 100 ml of dimethylformamide is dropped in so that the reaction temperature never exceeds −9° C. The batch is stirred on for 1 hour at −10° C. and then kept overnight at room temperature. The precipitated triethylamine hydrochloride is filtered off, the filtrate evaporated under a high vacuum at 40° C., the oily residue is taken up in 500 ml of ethyl acetate, washed with N-citric acid, N-sodium bicarbonate and saturated sodium chloride solution, dried, evaporated to about 40 ml and about 10 ml of petroleum ether are added. Overnight, the protected pentapeptide ester melting at 177°–178° C. crystallizes out.

In the thin-layer chromatogram on silica gel in chloroform+methanol (98:2) Rf=0.45, in toluene+acetate (7:3) Rf=0.57.

(9) DPC-Ser(tBu)-Thr(tBu)-Cys(TRI)-Val-Leu—OH

A solution of 2.830 g (2 mmols) of DPC-Ser(tBu)-Thr(tBu)-Cys(TRI)-Val-Leu-OMe in 60 ml of 75% dioxan is mixed with 3 ml of 2N-sodium hydroxide solution (6 mmols). After 1½ hours at room temperature the dioxan is evaporated under a water-jet vacuum at 40° C., then ethyl acetate and water are added and the whole is adjusted to a pH value of 3 at 0° C. with N-citric acid. The ethyl acetate phase is eashed with sodium chloride solution, dried and evaporated, to furnish a product which according to its thin-layer chromatogram on silica gel is uniform. Rf in chloroform+methanol (7:3)=0.40. Rf$_{45}$=0.55.

(10) H-Ser(tBu)-Thr(tBu)-Cys(TRI)-Val-Leu—OH

A solution of 2.22 g (2 mmols) of DPC-Ser(tBu)-Thr(tBu)-Cys(TRI)-Val-Leu—OH in 20 ml of methylenechloride is mixed with 12 ml of chloracetic acid in water [prepared from 75 g of chloracetic acid and 25 ml of water]. The clear solution is stirred for 15 minutes at room temperature, cooled to 0° C. and then 70 ml of water are added, adjusted with concentrated ammonia to pH=6.5, whereupon the product settles out. The aqueous solution is decanted and the residue triturated three times with water and lyophilized. On trituration with ether a white product is obtained which is unitary according to its thin-layer chromatogram. It is further used in this form.

In the thin-layer chromatogram on silica gel Rf$_{45}$=0.48; Rf$_{101}$=0.65; Rf$_{52}$=0.75.

(11) Z-Asn-Leu-OMe

A solution of 16.7 g of H-Leu-OMe and 46.0 g of Z-Asn-ONP in 100 ml of freshly distilled dimethylformamide is kept for 19 hours at 25° C., then 1.2 litres of water are added and the crystalline precipitate is suctioned off. The dipeptide derivative is dried under vacuum at 40° C. and then twice recrystallized from aqueous methanol. It melts at 180°–181° C. Optical rotation $[\alpha]_D^{20} = +9°$ (c=2.05 in chloroform).

(12) H-Asn-Leu-OMe

A solution of 15.0 g of Z-Asn-Leu-OMe in 400 ml of tertiary butanol+water (9:1) is hydrogenated in the presence of 2 g of palladium carbon (10% Pd). On completion of the hydrogenation the catalyst is suctioned off and the filtrate evaporated at 40° C. The residue is further used as it is.

(13) Z-Ser(tBu)-Asn-Leu-OMe

A solution of 8.90 g of H-Asn-Leu-OMe and 11.0 g of Z-Ser(tBu)-OH in 100 ml of freshly distilled dimethylformamide is cooled to 0° C. and mixed with 3.90 g of N-hydroxysuccinimide and 8.70 g of dicyclohexyl carbodiimide. After allowing the batch to stand for 30 minutes at 0° C. and then for 18 hours at 25° C. the precipitated dicyclohexylurea is suctioned off and the filtrate poured into 800 ml of ice water. The resulting crystalline precipitate is dried under vacuum at 40° C. and then recrystallized from aqueous methanol. The resulting analytically pure product - Z-Ser(tBu)-Asn-Leu-OMe -melts at 202°-205° C. Optical rotation $[\alpha]_D^{20} = 18°$ (c=1.05 in glacial acetic acid).

(14) H-Ser(tBu)-Asn-Leu-OMe

A solution of 6.3 g of Z-Ser(tBu)-Asn-Leu-OMe in 600 ml of methanol is hydrogenated in the presence of 1.2 g of palladium carbon (10% Pd). After 1¼ hours the catalyst is suctioned off and the filtrate evaporated to dryness at 30° C. bath temperature under vacuum. The resulting crystalline tripeptide derivative reveals in the thin-layer chromatogram on silica gel plates in chloroform+methanol (90:10) an Rf value of 0.11.

(15) BOC-Cys(TRI)-Ser(tBu)-Asn-Leu-OMe 5.0 Grams of H-Ser(tBu)-Asn-Leu-OMe and 6.7 g of BOC-Cys(TRI)-ONP are dissolved in 30 ml of freshly distilled dimethylformamide and the yellow solution is kept for 42 hours at 20° C., the product precipitated by the addition of ½ litre of ice water and the precipitate is suctioned off, dissolved in ethyl acetate and the solution is washed with 5% citric acid solution and then with water. It is then freed from pnitrophenol by being washed, while cooling with ice, 5 times with a mixture of 1 part by volume each of 5% potassium carbonate solution and 5% potassium bicarbonate solution and then with water. When the ethyl acetate solution is dried and evaporated it leaves a resinous product which is reprecipitated four times from acetone and petroleum ether. The resulting tetrapeptide derivative, which is thus obtained as a solid powder, melts at 181°-182° C. Optical rotation $[\alpha]_D^{20} = -11$ (c=2.09 in methanol).

In the thin-layer chromatogram on silica gel plates the $Rf_{43A}=0.57$; Rf in ethyl acetate=0.10; Rf in toluene+acetone (7:3)=0.05; Rf in chloroform+methanol (9:1) is 0.45.

(16) BOC-Cys(TRI)-Ser(tBu)-Asn-Leu-NH—NH₂

A solution of 7.0 g of BOC-Cys(TRI)-Ser(tBu)-Asn-Leu-OMe in 70 ml of methanol is cooled to 0° C. and then mixed with 7 ml of hydrazine hydrate. After 16 hours at 2° C. an ice-cold solution of 600 ml of 2N-acetic acid is added, the gelatinous precipitate thoroughly triturated, suctioned off and washed with much water until it runs neutral. The resulting powder is dried under vacuum at 40° C. and then suspended in 100 ml of acetonitrile, triturated, suctioned and dried under vacuum at 40° C. The resulting BOC-Cys(TRI)-Ser(tBu)-Asn-Leu hydrazide melts at 216°-218° C.

In the thin layer chromatography on silica gel plates it reveals the following Rf values: Rf=0.55 in dioxan+- water (98:2); Rf=0.52 in chloroform+methanol (8:2); $Rf_{102E}=0.70$.

(17) BOC-Cys(TRI)-Ser(tBu)-Asn-Leu-Ser(tBu)-Thr(tBu)-Cys(TRI)-Val-Leu—OH 1.075 Grams (1.26 mmols) of BOC-Cys(TRI)-Ser(tBu)-Asn-Leu-NH-NH₂ in 15 ml of dimethylformamide are mixed at −15° C. with 1.71 ml of hydrochloric acid in ethyl acetate (1.84 N; 3.15 mmols) and 0.174 ml (1.51 mmols) of tertiary butylnitrite [1.74 ml of a solution of 1 ml of tertiary butylnitrite made up to 10 ml with dimethylformamide]. The solution is stirred for 15 minutes at −10° C., and then a solution cooled at −12° C. of 1.104 g (1.26 mmols) of H-Ser(tBu)-Thr(tBu)-Cys(TRI)-Val-Leu—OH and 0.61 ml (4.41 mmols) of triethylamine in 15 ml of dimethylformamide is dropped in. The reaction mixture is stirred for 1 hour at −10° C. and then for 4 hours at room temperature. On evaporation to a small volume under a high vacuum and addition of water a pulverulent product is obtained which is twice triturated with water and then dried in a high vacuum over potassium hydroxide solution. This crude product is purified by redissolution from methanol. From a methanolic solution saturated at 50° C. a white powder settles out overnight at 0° C.; in thin-layer chromatography it is found to be unitary.

In the thin-layer chromatogram on silica gel $Rf_{43C}=0.54$; $Rf_{121A}=0.65$; $Rf_{45}=0.50$; $Rf_{70}=0.75$; Rf in chloroform+methanol (8:2) is 0.40.

EXAMPLE 2

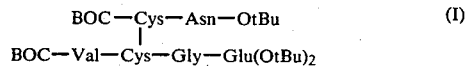

172 mg (0.2 mmol) of BOC-Val-Cys(TRI)-Gly-Glu(OtBu)₂ and 128 mg of BOC-Cys(TRI)-Asn-OtBu in 5 ml of ethyl acetate and 2 ml of methanol are mixed with 254 mg (1 mmol) of iodine in 5 ml of methanol and the solution is kept for 1 hour at room temperature, then decolorized at 0° C. with N-thiosulphate solution; the reaction mixture is taken up in 200 ml of ethyl acetate and three times washed with water. When the ethyl acetate solution is dried with sodium sulphate and concentrated, crystalline [BOC-Cys-Asn-OtBu]₂, melting at 194°-196° C. settles out in a yield of 32 g and is filtered off. The filtrate is evaporated to dryness and the residue twice triturated with petroleum ether. When the insoluble residue is subjected to column chromatography on silica gel, it furnishes 90 mg of product I, which reveals in the thin-layer chromatogram on silica gel Rf=0.25 in chloroform+methanol (95:5), an Rf=0.30 in toluene+acetone (1:1).

The second product obtained by column chromatography is 54 mg of [BOC-Val-Cys-Gly-Glu(OtBu)]₂. Rf (on silica gel) in chloroform+methanol (9:1)=0.55. The above-mentioned crystalline dimer, melting at 194°-196° C., reveals the following Rf values (on silica gel): in chloroform+methanol (9:1) Rf=0.25; in toluene+acetone (1:1) Rf=0.18.

The two starting peptides are accessible as follows:

(1) Z-Asn-OtBu 300 ml of isobutylene is injected at −30° C. into a solution of 32 g (120 mmols) of Z-Asn—OH in 600 ml of dioxan, then 12 ml of concentrated sulphuric acid are added and the flask is closed and kept for 20 hours at 0° C. while being occasionally shaken, whereby a clear solution is obtained, which is substantially freed from excess isobutylene at room temperature. The resulting solution is mixed at 0° C. with an aqueous solution of 44 g of potassium bicarbonate, then concentrated to a small volume and taken up in ethyl acetate. The organic phase is washed with N-bicarbonate and then with water until it runs neutral. The ethyl acetate solution is dried with sodium sulphate and concentrated, whereupon the product begins to crystallize out. n-Hexane is added and the product filtered off; it melts at 100°-102° C. Optical rotation $[\alpha]_D^{23} = -16°$ (c=2 in methanol). In the thin-layer chromatogram on silica gel the Rf value in toluene+acetone (7:3) is 0.27, in ethyl acetate Rf=0.43.

(2) H-Asn-OtBu 23.6 Grams (73.2 mmols) of Z-Asn-OtBu in 200 ml of ethyl acetate are hydrogenated in the presence of 2 g of palladium carbon (10% Pd) until, after 1 hour, hydrogen is no longer absorbed. The catalyst is filtered off and the filtrate concentrated, whereupon the product, melting at 96°-98° C., crystallizes out. Optical rotation $[\alpha]_D^{20} = +2°$ (c=2.1 in methanol). In the thin-layer chromatogram on silica gel the $Rf_{52}=0.30$; $Rf_{45}=0.50$.

(3) BOC-Cys(TRI)-Asn-OtBu

A mixture of 18.52 g (40 mmols) of BOC-Cys(TRI)—OH and 5.6 ml (40 mmols) of triethylamine in 200 ml of tetrahydrofuran is mixed at −10° C. with 5.32 ml (40 mmols) of isobutyl chlorocarbonate and the whole is stirred at this temperature for 10 minutes. Then a solution, cooled at −10° C., of 7.52 g (40 mmols) of H-Asn-OtBu in 150 ml of tetrahydrofuran is dropped in and the mixture is kept for 1 hour at −10° C. and then overnight at room temperature. The precipitated triethylamine hydrochloride is then filtered off, the filtrate evaporated to dryness and the residue is taken up in ethyl acetate and washed with N-citric acid, N-sodium bicarbonate solution and water. On concentration of the ethyl acetate solution and addition of petroleum ether the product, melting at 155°-157° C., crystallizes out. Optical rotation $[\alpha]_D^{23} = +34°$ (c=2.1 in chloroform). Rf in the thin-layer chromatogram on silica gel in toluene+acetone (1:1)=0.45, in chloroform+methanol (95:5)=0.33; $Rf_{43A}=0.65$.

(4) Z-Gly-Glu(OtBu)₂

A solution of 23.2 g (0.11 mol) of Z-Gly—OH and 15.34 ml (0.11 mol) of triethylamine in 200 ml of tetrahydrofuran is mixed at −10° C. with 14.97 ml (0.11 mol) of isobutyl chlorocarbonate and the whole is kept for 10 minutes at −10° C. A mixture of 28.52 g (96.5 mmols) of H-Glu(OtBu)₂,HCl and 13.5 ml (96.5 mmols) of triethylamine hydrochloride in 300 ml of tetrahydrofuran is filtered off the triethylamine hydrochloride, cooled to −10° C. and the above solution is the dropped in at −10° C. The batch is stirred for 1 hour at −10° C. and then for 2 hours at room temperature, the precipitated triethylamine hydrochloride is filtered off and the filtrate evaporated to dryness. The resulting oil is kept up in ethyl acetate and washed with N-citric acid, N-sodium bicarbonate and water. On evaporation of the ethyl acetate the peptide derivative is obtained which crystallizes from ethyl acetate+n-hexane and melts at 74°-76° C. Optical rotation $[\alpha]_D^{23} = -17°$ (c=2.2 in methanol). In the thin-layer chromatogram on silica gel the Rf value in toluene+acetone (7+3) is 0.50.

(5) H-Gly-Glu(OtBu)₂

2.7 Grams (6 mmols) of Z-Gly-Glu(OtBu)₂ in 30 ml of ethyl acetate are hydrogenated in the presence of 250 mg of palladium carbon (10% Pd). After 4 hours the absorption of hydrogen ceases. The catalyst is filtered off and the solution evaporated. The product is obtained as an oil which is unitary according to its thin-layer chromatogram. The Rf values (on silica gel) are: in toluene+acetone (7:3)=0.27; in chloroform+methanol (9:1)=0.37; $Rf_{43A}=0.50$.

(6) TRI-Cys(TRI)-Gly-Glu(OtBu)₂

26.6 Grams (44 mmols) of TRI-Cys(TRI)-OH and 13.9 g (44 mmols) of H-Gly-Glu(OtBu)₂ in 350 ml of ethyl acetate are mixed at 0° C. with 9.06 g (44 mmols) of dicyclohexyl carbodiimide, the whole is stirred for 2 hours at 0° C. and then kept overnight in a refrigerator. The precipitated dicyclohexylurea is then filtered off and the filtrate washed with N-citric acid, N-sodium bicarbonate and water, dried and evaporated. The product crystallizes from ethyl acetate+n-hexane and melts at 107°-108° C. Optical rotation $[\alpha]_D^{23} = +8°$ (c=2.0 in methanol). In the thin-layer chromatogram on silica gel in toluene+acetone (7:3) Rf=0.70, in chloroform+methanol (98:2) Rf=0.78.

(7) H-Cys(TRI)-Gly-Glu(OtBu)₂

3.156 g (3.5 mmols) of TRI-Cys(TRI)-Gly-Glu(OtBu)₂ in 20 ml of glacial acetic acid are mixed at temperature with 5 ml of water so that the precipitate formed always dissolves again. After about 10 minutes the batch turns turbid and a precipitate forms. The batch is stirred for 1 hour, then 15 ml of water are added and the mixture is filtered. The filtrate is evaporated at 40° C. in a high vacuum, the residue taken up in ethyl acetate and at 0° C. washed with 0.5N-sodium bicarbonate solution and with water and evaporated. The resulting foam is triturated with petroleum ether. In the thin-layer chromatogram on silica gel in chloroform+methanol (95:5) the product reveals an Rf value of 0.40, in toluene+acetone (1:1) Rf=0.55; $Rf_{43A}=0.60$.

(8) BOC-Val-Cys(TRI)-Gly-Glu(OtBu)₂

7.17 Grams (33 mmols) of BOC-Val-OH and 4.62 ml of triethylamine (33 mmols) in 80 ml of ethyl acetate are mixed at −10° C. with 4.4 ml (33 mmols) of isobutyl chlorocarbonate and the whole is stirred for 10 minutes at −10° C. A solution, cooled at −10° C., of 21.92 g (33 mmols) of H-Cys(TRI)-Gly-Glu (OtBu)₂ in 400 ml of ethyl acetate is dropped in and the mixture is maintained for 1 hour at −10° C. and then for 10 hours at room temperature. The batch is then evaporated to dryness, the residue triturated with 2×200 ml of water, and dried over phosphorus pentoxide. The residue is dissolved in 450 ml of hot methanol. The product crystallizes overnight at 0° C. Melting point, 213°-215° C. $[\alpha]_D^{23} = +19°$ (c=2.2 in chloroform). In the thin-layer chromatogram on silica gel in the system cyclohexane-ethyl acetate (1:1) the Rf value is 0.18; in the system toluene: acetone (1:1), Rf=0.65.

EXAMPLE 3

127 mg (0.5 mmol) of iodine in 2.5 ml of methanol are added to 172 mg (0.2 mmol) of BOC-Val-Cys(TRI)-Gly-Glu (OtBu)₂ in 5 ml of ethyl acetate and 2 ml of methanol and the reaction mixture is allowed to stand at room temperature for 1 hour. The solution is then discolored at 0° C. with 1N-thiosulfate, then dissolved in 200 ml of ethyl acetate and washed three times with water. The product obtained on evaporation of the ethyl acetate is triturated twice with petroleum ether. [BOC-Val-Cys-Gly-Glu(OtBu)$_2$]$_2$, which is insoluble in petroleum ether, is unitary according to thin-layer chromatography.

Yield, 123 mg (100%).

EXAMPLE 4

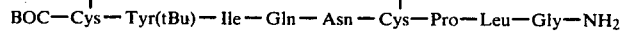

BOC—Cys—Tyr(tBu)—Ile—Gln—Asn—Cys—Pro—Leu—Gly—NH$_2$ 500 mg of BOC-Cys(TRI)-Tyr(tBu)-Ile-Gln-Asn-Cys(TRI)-Pro-Leu-Gly-NH$_2$, dissolved in 100 ml of methanol are added dropwise in the course of 45 minutes to a solution of 620 mg of iodine in 150 ml of methanol while stirring vigorously at 25° C. Stirring is continued for another hour, the solution then cooled to 5° C. and discolored by the addition of 1.0N-aqeuous sodium thiosulfate solution. The solution is then concentrated to a volume of about 5 ml in a water-jet volume, and the product precipitated by the addition of much water. It is suctioned off and dried in vacuo over sodium hydroxide. For conversion into the free oxytocin the product is suspended in 5 ml of ice-cold concentrated hydrochloric acid and dissolved with stirring. After 10 minutes at 0° C. the solution is diluted with 20 ml of ice water, mixed with 5 ml of glacial acetic acid, filtered through a column of Merck ion exchange resin No. II, weakly basic, acetate form, and then rinsed with 20% acetic acid, and evaporated at 30° C. under vacuum. The residue is dissolved in water and the solution lyophilized. The resulting crude oxytocin may, if desired, be further purified by the process described by Yamashiro (Nature 201, p. 76 [1964]).

The protected nonapeptide derivative BOC-Cys(TRI)-Tyr(tBu)-Ile-Gln-Asn-Cys(TRI)-Pro-Leu-Gly-NH$_2$ used as starting material may be prepared thus:

(1) TRI-Cys(TRI)-Pro-Leu-Gly-NH$_2$

A solution of 30 g of H-Pro-Leu-Gly-NH$_2$ in 500 ml of freshly distilled dimethylformamide is cooled to 5° C. and then mixed with 70 g of TRI-Cys(TRI)-OH, 20 g of N-hydroxysuccinimide and 30 g of dicyclohexyl carbodiimide. After 30 minutes at 0° C. the batch is warmed to room temperature and then left to itself for 18 hours; the precipitated dicyclohexylurea is suctioned, the filtrate evaporated at 40° C. under a high vacuum and 1 liter of petroleum ether is added to the residue. The undissolved product is thoroughly triturated and the petroleum ether solution decanted. The residue insoluble in petroleum ether is taken up in ethyl acetate, washed at 0° C. with dilute citric acid, water, sodium bicarbonate solution and with water, dried with sodium sulphate and evaporated to dryness. The resulting crude tetrapeptide derivative TRI-Cys(TRI)-Pro-Leu-Gly-NH$_2$ is purified by being dissolved in methanol and filtered through a column of Sephadex LH-20. The resulting fractions are evaporated and tested for purity by thin-layer chromatography on silica gel plates in chloroform+methanol (99:1). The pure fractions are combined, evaporated and dried.

(2) H-Cys(TRI)-Pro-Leu-Gly-NH$_2$

To eliminate the N$^\alpha$-TRI group 5 g of TRI-Cys(TRI)Pro-Leu-Gly-NH$_2$ are dissolved in 100 ml of 80% acetic acid and the solution is heated for 1 hour at 35° C., then mixed with 100 ml of water and kept for 5 hours at 0° C. The crystals of the precipitated triphenylcarbinol are then suctioned off, the filtrate evaporated to dryness and the residue dried at 30° C. in a high vacuum. For conversion into the free base the H-Cys(TRI)-Pro-Leu-Gly-NH$_2$, obtained as the acetate, is dissolved in chloroform, the solution washed with dilute sodium bicarbonate solution, dried over sodium sulphate and evaporated.

(3) Z-Tyr(tBu)-Ile-Gln-Asn-OH

A solution of 4.05 g of H-Ile-Gln-Asn-OH in 70 ml of water and 1.5 ml of triethylamine is mixed with 200 ml of dimethylformamide. Then 8 g of Z-Tyr(tBu)-p-nitrophenyl ester [prepared from Z-Tyr(tBu)-OH and p-nitrophenol by means of dicyclohexyl carbodiimide; melting at 88°–89° C. from aqueous methanol] are added and the whole is kept for 72 hours at room temperature, then concentrated under vacuum at 40° C. to about 20 ml, 100 ml of 0.5N-sodium bicarbonate solution and 200 ml of ether are added, the ethereal solution is separated and the aqueous phase cooled in ice. After acidification with 2N-hydrochloric acid the precipitated Z-Tyr(tBu)-Ile-Gln-Asn-OH is suctioned off and washed with ice water. For purification it is reprecipitated from its dimethylformamide solution with ether.

(4) H-Tyr(tBu)-Ile-Gln-Asn-OH

A solution of 1.2 g of the tetrapeptide derivative obtained sub (3) in 50 ml of 90% acetic acid is hydrogenated in the presence of 0.5 g of palladium carbon (10% Pd). On completion of the hydrogenation the catalyst is suctioned off, the filtrate evaporated to dryness under vacuum and the residue dried at 40° C. under a high vacuum.

(5) BOC-Cys(TRI)-Tyr(tBu)-Ile-Gln-Asn-OH

The product obtained sub (4) is suspended in 35 ml of dimethylformamide and 0.5 ml of triethylamine and dissolved by adding water. Then 1.0 g of BOC-Cys(TRI)-p-nitrophenyl ester is added and the reaction mixture kept for 48 hours at 28° C., then concentrated under a high vacuum at 35° C., the residue mixed with 100 ml of ice-cold N-hydrochloric acid and the crude pentapeptide derivative is suctioned off, washed with ice water, dried and repeatedly reprecipitated from dimethylformamide+ether. For further purification the product is dissolved in methanol and chromatographed on a column of Sephadex LH-20.

(6) BOC-Cys(TRI)-Tyr(tBu)-Ile-Gln-Asn-Cys(TRI)-Pro-Leu-Gly-NH$_2$ 2.1 Grams of the tetrapeptide derivative obtained sub (2) and 3.3 g of BOC-Cys(TRI)-Tyr(tBu)-Ile-Gln-Asn-OH are dissolved in 50 ml of dimethylformamide with addition of 1 g of N-hydroxysuccinimide. The solution is cooled to −20° C., mixed with 0.9 g of dicyclohexyl carbodiimide and kept for 2 hours at −20° C. and then for 48 hours at room temperature, during which after 6, 12 and 18 hours another 200 mg each of dicyclohexyl carbodiimide are added. The precipitated dicyclohexyl carbodiimide is filtered off, the filtrate concentrated to a small volume under a high vacuum at a bath temperature of 40° C. and the nonapeptide derivative is precipitated with ether. The powder is suctioned off, dried, triturated with water, once more suctioned off and dried. The resulting crude BOC-Cys(TRI)-Tyr(tBu)-Ile-Gln-Asn-Cys(TRI)-Pro-Leu-Gly-NH$_2$ is purified by counter-current distribution in the same system as described in Example 1.

EXAMPLE 5

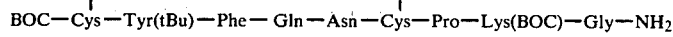
BOC—Cys—Tyr(tBu)—Phe—Gln—Asn—Cys—Pro—Lys(BOC)—Gly—NH$_2$

While vigorously stirring a solution of 1120 mg of iodine in 500 ml of methanol at room temperature it is mixed dropwise within 45 minutes with a solution of 800 mg of BOC-Cys(TRI)-Tyr(tBu)-Phe-Gln-Asn-Cys(TRI)-Pro-Lys(BOC)-Gly-NH$_2$ in 500 ml of methanol. The solution is then cooled to 2° C. and decolorized by dropping in aqueous N-sodium thiosulphate solution, then concentrated to a small volume in a water-jet vacuum at 30° C. bath temperature and the product is precipitated again by adding much water; it is suctioned off and dried in a vacuum desiccator.

For conversion into lysine[8]-vasopressin the BOC-

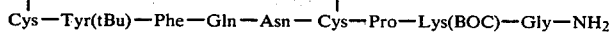
Cys—Tyr(tBu)—Phe—Gln—Asn—Cys—Pro—Lys(BOC)—Gly—NH$_2$ is dissolved with stirring in 10 ml of ice-cold concentrated hydrochloric acid. After 10 minutes at 0° C. the batch is diluted with 50 ml of ice water and 5 ml of glacial acetic acid are added. The batch is then filtered through a column of Merck ion exchange resin No II, (weekly basic, acetate form) and the eluate evaporated to dryness.

The protected nonapeptide derivative BOC-Cys(-TRI)-Tyr(tBu)-Phe-Gln-Asn-Cys(TRI)-Pro-Lys(-BOC)-Gly-NH$_2$ used as starting material is accessible, as described for the protected nonapeptide amide in Example 4, by condensing BOC-Cys(TRI)-Tyr(tBu)-Phe-Gln-Asn-OH with H-Cys(TRI)-Pro-Lys(BOC)-Gly-NH$_2$ in the presence of dicyclohexyl carbodiimide and N-hydroxysuccinimide. The intermediates may likewise be prepared in an analogous manner.

EXAMPLE 6

BOC-Cys-Phe-Phe-Gln-Asn-Cys-Pro-Lys(BOC)-Gly-NH$_2$

This compound may be prepared by the process described in Example 5 from BOC-Cys(TRI)-Phe-Phe-Gln-Asn-Cys(TRI)-Pro-Lys(BOC)-Gly-NH$_2$ and converted into PHe[2], Lys[8]-vasopressin.

EXAMPLE 7

1524 g of BOC-Cys(TRI)-Gly-Glu(OtBu)$_2$ and 5.08 mg of iodine in 25 ml of methanol are allowed to react for 1 hour at room temperature. At 0° C. the reaction solution is decolorized by dropping in aqueous N-sodium thiosulphate solution and the product is precipitated with 50 ml of water. The dried crude product is triturated with 3×10 ml of petroleum ether. Crystallization of the residue from ethyl acetate+petroleum ether furnishes 945 mg (=91% of theory) of [BOC-Cys-Gly-Glu(OtBu)$_2$]$_2$ melting at 150°–152° C. Rf=0.60 (chloroform+methanol 9:1).

EXAMPLE 8

762 mg (1.0 mmol) of BOC-Cys(TRI)-Gly-Glu(Ot-Bu)$_2$ and 634 mg (1.0 mmol) of BOC-Cys(TRI)-Asn-OtBu are reacted with 508 mg of iodine (2.0 mmols) and then worked up as described in Example 7. The crude product reveals in the thinlayer chromatogram on silica gel in chloroform+methanol (9:1) three spots: Rf=0.60([BOC-Cys-Gly-Glu(OtBu)$_2$]$_2$=I), 0.25 ([BOC-Cys-Asn-OtBu]$_2$=II) and 0.45

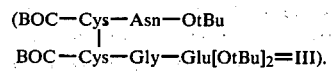
(BOC—Cys—Asn—OtBu
BOC—Cys—Gly—Glu[OtBu]$_2$=III).

Separation can be achieved by counter-current distribution in methanol+0.1 amonium acetate+chloroform+carbon tetrachloride (4:2:1:3). After 100 steps the product II is found in the elements 56–76 (r$_{max}$=65; K=1.85), which are emptied, fresh bottom phase is poured in and another 100 steps are carried out. Product III is now found in tubes 8–25 (r$_{max}$=16; K=0.09) and product I in elements 0–5. Evaporation of these fractions and sublimation of ammonium acetate furnishes the three compounds in a thin-layer chromatographically pure form:

Product I melts after recrystallization from ethyl acetate+petroleum ether at 150°–152° C. Yield: 225 mg (statistically: 260 mg)

Product II melts after recrystallization from methanol+ether at 194–196; yield: 162 mg (statistically: 195 mg)

Product III is amorphous. Yield: 463 mg.

When the reaction is performed with 1 mmol of BOC-Cys(TRI)-Gly-Glu(OtBu)$_2$, 2 mmols of BOC-Cys(TRI)-Asn-OtBu and 3 mmols of iodine, 580 mg of product III are isolated (statistically: 606 mg).

EXAMPLE 9

To 254 mg (1 mmol) of iodine in 5 ml of glacial acetic acid is added a solution of 380 mg (0.5 mmol) of BOC-Cys(TRI)-Gly-Glu(OtBu)$_2$ and 45 mg (0.65 mmol) of (anhydrous) sodium acetate in 5 ml of glacial acetic acid, and the mixture is stirred at room temperature for one hour. By addition of 1 N sodium thiosulfate (1.7 ml) the brown solution is discolored. Another 5 ml of glacial acetic acid are added and the whole is lyophilized. The resulting powder is dissolved in water, filtered, and the residue washed well with water. After drying over phosphorus pentoxide and recrystallization from a mixture of ethyl acetate and petroleum ether, 205 mg (80%) of [BOC-Cys-Gly-Glu(OtBu)$_2$]$_2$ of melting point 151°–152° C. are obtained.

EXAMPLE 10

85 mg of iodine are added to a solution of 260 mg of H-Cys(TRI)-Gly-Glu-OH, trifluoroacetate in 8 ml of 50% by volume of aqueous methanol, and the mixture is stirred for 30 minutes. Then it is concentrated to 3 ml in a rotary evaporator at 30° C. and 3 ml of water and 5 ml of ether are added. The aqueous phase is filtered through a column of a weakly basic ion exchanger (Merck Nr. II, acetate). Lyophilisation of the eluate yields a white powder of

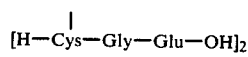

[H—Cys—Gly—Glu—OH]$_2$ which is pure according in thin layer chromatography on cellulose: Rf=0.40 in the system n-butanol-pyridine-formic acid-water (34:24:12:30, Vol.) In the electrophoresis on cellulose (90 minutes, 16 Volt/cm) the product migrates 5.5 cm to the cathode at pH 1.9, and 3.3 cm to the anode at pH 4.0.

The starting material can be prepared as follows: 460 mg of BOC-Cys(TRI)-Gly-Glu(OtBu)$_2$ are dissolved at 0° C. in 5 ml of absolute trifluoracetic acid. The solution is allowed to stand for 30 minutes at 20° C. and then evaporated in a rotary evaporator at 30° C. The remaining oil is titrated with 20 ml of ether to a white powder which is dried over sodium hydroxide. In the thin layer chromatogram on cellulose Rf=0.75 in the system indicated above.

We claim:

1. Process for the manufacture of cystine-containing peptides and derivatives thereof from corresponding cysteine-containing aminoacid sequences in which the mercapto groups are protected by trityl groups, wherein the aminoacid sequence(s) containing the cysteine residues to be combined is (are) treated with iodine in a solvent in which both iodine and the peptide are at least partically soluble.

2. Process as claimed in claim 1, wherein the reaction is performed at room temperature.

3. Process as claimed in claim 1, wherein the reaction is performed in a lower alkanol.

4. Process as claimed in claim 3, wherein the reaction is performed in methanol.

5. Process as claimed in claim 1, wherein the reaction is performed in glacial acetic acid.

6. Process as claimed in claim 1, wherein the reaction is performed in a mixture of lower alkanol and another organic solvent.

7. Process as claimed in claim 1, wherein the starting material is a cysteine-containing aminoacid sequence which contains both cysteine residues so that a cyclic peptide is formed by means of the disulfide bridge.

8. Process as claimed in claim 1, wherein the starting material is an aminoacid sequence containing but one cysteine residue, so that the dimer having a disulfide bridge is formed.

9. Process as claimed in claim 1, wherein two different aminoacid sequences are used as starting material, each containing one cysteine residue, so that two different aminoacid sequences linked by a disulfide bridge are formed.

* * * * *